(12) United States Patent
Bourgeois et al.

(10) Patent No.: US 8,093,432 B2
(45) Date of Patent: Jan. 10, 2012

(54) PROCESSES FOR EPIMERIZING CYCLOHEXENYL KETONES WITH SUBSEQUENT ALDOL CONDENSATION TO PRODUCE FRAGRANCE COMPOUNDS

(75) Inventors: Daniel Martin Bourgeois, Mason, OH (US); Gregory Scot Miracle, Hamilton, OH (US); Phillip John Porter, Mason, OH (US); Eva Boros, Sulzbach am Taunus (HU); Kenneth Richard Seddon, Donaghadee (GB); Harambage Quintus Nimal Gunaratne, Belfast (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/641,786

(22) Filed: Dec. 18, 2009

(65) Prior Publication Data
US 2011/0152575 A1    Jun. 23, 2011

(51) Int. Cl.
*C07C 45/67* (2006.01)
(52) U.S. Cl. .......................... 568/343; 568/349; 568/378
(58) Field of Classification Search .................. 568/343, 568/349, 378
See application file for complete search history.

(56) References Cited

U.S. PATENT DOCUMENTS

| 4,198,309 A | 4/1980 | Granda et al. |
| 4,334,098 A | 6/1982 | Mookherjee et al. |
| 6,573,405 B1 | 6/2003 | Abbott et al. |

OTHER PUBLICATIONS

PCT International Search Report, date mailed Mar. 4, 2010, 14 pages.
Ayyar, et al., Synthesis of δ—Damascone [trans—1-(2,6,6—Trimethylclohex-3-enyl) but-2-en-1-one] and β-Damascenone [trans-1-(2,6,6—Trimethylcyclohexa-1,3-dienyl) but-2-en-1-one] *Journal of the Chemical Society Perkin Trans.*, 1975, 1, pp. 1727-1736.
Abbott, Andrew P., et al., "Quaternary ammonium zinc- or tin-containing ionic liquids: water insensitive, recyclable catalysts for Diels-Alder reactions," *Green Chemistry*, vol. 4, pp. 24-26., 2002.
Dyson, Paul J., et al., "Effect of Lewis acis on the Diels-Alder reaction in ionic liquids with different activation modes," *Journal of Physical Organic Chemistry*, vol. 21, pp. 264-270, 2008.
Kumar, Anil, et al., "Converting exo-Selective Diels-Alder Reaction to endo-Selective in Chloroaluminate Ionic Liquids," *The Journal of Organic Chemistry*, 2004, 4, pp. 1419-1420.
Lee, C. W.a, "Diels-Alder Reactions in Chloroaluminate Ionic Liquids: Acceleration and Selectivity Enhancement," *Tetrahedron Letters*, Elsevier, Amsterdam, vol. 40, pp. 2461-2464, 1999.
U.S. Appl. No. 12/641,818, filed Dec. 18, 2009, David Martin Bourgeois, et al.

*Primary Examiner* — Sikarl Witherspoon
(74) *Attorney, Agent, or Firm* — Stephen T. Murphy; Steven W. Miller; Leonard W. Lewis (57) ABSTRACT

The present disclosure describes processes for the epimerization of a cyclohexene comprising the steps of providing to a reactor a first isomer of a 1-(2-alkyl-3-cyclohexen-1-yl)-alkanone compound according to Formula I

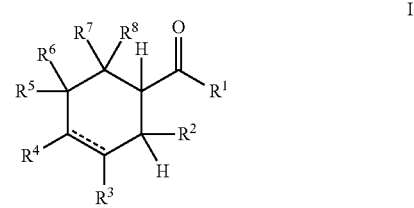

wherein $R^1$ ad $R^2$ are each independently $C_1$-$C_4$ alkyl, and $R^3$, $R^4$, $R^5$, $R^6$, $R^7$, and $R^8$ are each independently selected from the group consisting of H and $C_1$-$C_4$ alkyl; and epimerizing the first isomer of the 1-(2-alkyl-3-cyclohexen-1-yl)-alkanone with a metal alkoxide base to form a second isomer of the 1-(2-alkyl-3-cyclohexen-1-yl)-alkanone.

21 Claims, 1 Drawing Sheet

Fig. 1

PROCESSES FOR EPIMERIZING CYCLOHEXENYL KETONES WITH SUBSEQUENT ALDOL CONDENSATION TO PRODUCE FRAGRANCE COMPOUNDS

FIELD OF THE INVENTION

The present invention is related to single reactor processes for synthesizing substituted cyclohexanes useful as fragrance compounds utilizing an epimerization and aldol condensation of cyclic organic compounds.

BACKGROUND OF THE INVENTION

Perfume and aroma enhancing compounds are widely used as additives in the detergent and food industries. These compounds are used, for example, to augment or enhance the aromas of certain detergent compositions and perfumes, or to enhance the aroma and flavor characteristics of certain food or tobacco products among other products. Compounds with floral, fruity, woody, or other pleasing aroma are particularly desirable.

Many of these compounds have specific molecular features, such as the presence of a cyclic ring and/or a ketone, ester or other carbonyl derivative. For example, many fragrance components may include a substituted cyclohexene structure. These structures include, for example, various ionone isomers, damascone isomers, cyclogeranate isomers, and irone isomers. Other cyclic fragrance compounds are also known.

The damascones, including α-damascone, β-damascone, and δ-damascone are examples of compounds having pleasing floral, fruity aromas used in the perfumery art. The damascone isomers differ in the position of the ring double bond as shown in Scheme 1.

Scheme 1

α-Damascone    β-Damascone

δ-Damascone

For example, trans,trans-δ-damascone is one of the most widely used fragrance additives in the detergent and food industries. Therefore, the industrial scale production of δ-damascone and other related compounds is of great interest.

The synthesis of damascones typically involves a three-step process: (1) a Diels-Alder cycloaddition of a diene and a dienophile to produce a mixture of cis- and trans-cycloadducts; (2) epimerization of the cis-cycloadduct to the trans-cycloadduct; and (3) an aldol condensation of the trans-cycloadduct using an aldehyde followed by the elimination of water to generate a damascone. These reactions are performed in three separate reaction processes. A process for synthesizing damascone is described in Ayyer et al., *Journal of the Chemical Society Perkin Trans.*, 1975, 1, 1727-1736.

1-(2,6,6-Trimethylcyclohex-3-en-1-yl)-ethanone is a useful compound as an intermediate for the synthesis of the damascones. 1-(2,6,6-Trimethylcyclohex-3-en-1-yl)-ethanone can be readily synthesized by a Diels-Alder reaction between 1,3-pentadiene (piperylene) and mesityl oxide to produce a mixture of cis- and trans-1-(2,6,6-trimethylcyclohex-3-en-1-yl)ethanone. Typically, the cycloadduct from the Diels-Alder cycloaddition is a mixture of cis-1-(2,6,6-trimethylcyclohex-3-en-1-yl)ethanone and trans-1-(2,6,6-trimethylcyclohex-3-en-1-yl)ethanone. Thus, further synthetic transformations are necessary to convert the Diels-Alder cycloadduct to δ-damascone.

The conventional epimerization and aldol condensation processes used to synthesize δ-damascone from the mixture of 1-(2,6,6-trimethylcyclohex-3-en-1-yl)ethanone cycloadducts suffer from low yields and lack of control over the stereochemistry of the products. On the industrial scale, these reactions are problematic because of high reaction dilutions, large volumes of solvents, large reaction vessels, long reaction times, complex workup requirements, several extraction and drying steps, low atom efficiency, and low yields.

Therefore, a more commercially viable production of damascone isomers and other substituted cyclohexene based perfume components is necessary.

SUMMARY OF THE INVENTION

The present disclosure provides processes for converting cyclohexene compounds into compounds suitable for use as fragrance and perfume components. In specific embodiments, processes for the production of δ-damascone from 1-(2,6,6-trimethylcyclohex-3-en-1-yl)ethanone in a single reactor procedure are disclosed.

According to one embodiment, the present disclosure provides a process for the epimerization of a substituted cyclohexene comprising the steps of providing to a reactor a first isomer of a 1-(2-alkyl-3-cyclohexen-1-yl)-alkanone compound according to Formula I:

I and epimerizing the first isomer of the 1-(2-alkyl-3-cyclohexen-1-yl)-alkanone with a metal alkoxide base to form a second isomer of the 1-(2-alkyl-3-cyclohexen-1-yl)-alkanone. According to Formula I, $R^1$ and $R^2$ are each independently $C_1$-$C_4$ alkyl, and $R^3$, $R^4$, $R^5$, $R^6$, $R^7$, and $R^8$ are each independently selected from the group consisting of H and $C_1$-$C_4$ alkyl.

According to another embodiment, the present disclosure provides a process for producing an aldol condensation product comprising the steps of epimerizing a first cis/trans isomer of a 1-(2-alkyl-3-cyclohexen-1-yl)-alkanone according to Formula I:

with potassium tert-butoxide to form a second cis/trans isomer of the 1-(2-alkyl-3-cyclohexen-1-yl)-alkanone; and condensing the second isomer of the 1-(2-alkyl-3-cyclohexen-1-yl)-alkanone with an aldehyde followed by elimination of water to form a first aldol condensation product. According to Formula I, $R^1$ and $R^2$ are each independently $C_1$-$C_4$ alkyl, and $R^3$, $R^4$, $R^5$, $R^6$, $R^7$, and $R^8$ are each independently selected from the group consisting of H and $C_1$-$C_4$ alkyl.

According to still another embodiment, the present disclosure provides for a single reactor process for the production of a cyclohexene product comprising the steps of epimerizing a 1,2-cis-isomer of a 1-(2-alkyl-3-cyclohexen-1-yl)-alkanone with potassium tert-butoxide to form a 1,2-trans-isomer of the 1-(2-alkyl-3-cyclohexen-1-yl)-alkanone; and condensing the 1,2-trans-isomer of the 1-(2-alkyl-3-cyclohexen-1-yl)-alkanone with an aldehyde followed by elimination of water to form a first aldol condensation product, wherein the epimerizing step and the condensing step are performed in a single reactor.

According to another embodiment, the present disclosure provides for a perfume composition comprising (±)-δ-damascone having greater than 82% by weight of the trans-ring isomer. The (±)-δ-damascone perfume composition may be incorporated into a detergent composition, a fine fragrance composition, or an air freshener composition.

BRIEF DESCRIPTION OF DRAWINGS

The various non-limiting embodiments of this application may be better understood when read in conjunction with the following drawing FIGURE.

DETAILED DESCRIPTION OF THE INVENTION

Definitions

As used herein, the term "comprising" means various components conjointly employed in the preparation of the compositions of the present disclosure. Accordingly, the terms "consisting essentially of" and "consisting of" are embodied in the term "comprising".

As used herein, the articles including "the", "a" and "an" when used in a claim or in the specification, are understood to mean one or more of what is claimed or described.

As used herein, the terms "include", "includes" and "including" are meant to be non-limiting.

As used herein, the term "plurality" means more than one.

As used herein, the term "Diels-Alder cycloaddition" describes a [4+2] cycloaddition between a diene component having a conjugated 1,3-diene functionality and a dienophile component having a reactive double or triple bond. Reactions via step-wise or concerted mechanisms are included within this term.

As used herein, the terms "Diels-Alder cycloadduct" and "Diels-Alder adduct" describe the cyclohexene product resulting from a Diels-Alder cycloaddition.

As used herein, the term "epimerization" describes the transformation of a first epimer to a second epimer. Epimerization may be accomplished by a deprotonation-deprotonation approach.

As used herein, the term "aldol reaction" includes a reaction of the enolate of a carbonyl compound, such as a ketone or an aldehyde, with a second carbonyl compound, such as a ketone or an aldehyde, to form the aldol addition product (a β-hydroxycarbonyl compound).

As used herein, the term "aldol condensation" describes the reaction of the enolate of a carbonyl compound, such as a ketone or an aldehyde, with a second carbonyl compound, such as a ketone or an aldehyde, to form the aldol addition product (a β-hydroxycarbonyl compound) followed by the elimination of water to form an unsaturated carbonyl compound.

As used herein, the term "aldol condensation product" describes the product resulting from an aldol condensation reaction.

As used herein, the term "elimination of water" includes the loss of a hydroxy moiety from a first atom and a hydrogen atom from an adjacent atom, combined with the formation of a pi-bond between the first atom and the adjacent atom. The "elimination of water" includes the elimination of the elements of water (i.e., the elimination of hydroxy and a hydrogen) where the elements of water do not necessarily combine to form a molecule of water during the elimination.

As used herein, the phrase "performed in a single reactor" means that the two or more reaction processes are performed in one or more reactors without an intermediate isolation step. In certain examples, the two or more reaction processes may also be performed without an intermediate workup or quenching step.

Unless otherwise noted, all component or composition levels are in reference to the active portion of that component or composition, and are exclusive of impurities, for example, residual solvents or by-products, which may be present in commercially available sources of such components or compositions.

In specific chemical structures displayed herein where stereochemistry is denoted using solid and dashed wedge-shaped bonds, the structures encompass all stereochemical arrangements of the chemical structures unless specifically limited to a single enantiomers or specific diastereomers.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The Epimerization Process

The present disclosure is related to processes for producing substituted cyclohexanes from cyclic organic compounds useful in a variety of applications, such as fragrance components, by novel epimerization and aldol condensation processes. In particular, according to various embodiments, a first isomer of a cyclohexenyl alkyl ketone may be epimerized to a second isomer by reaction with a metal alkoxide base; and the second isomer may be condensed with a carbonyl compound, such as an aldehyde or ketone, followed by the elimination of water to form a first aldol condensation product. The processes disclosed herein may have certain advantages over conventional approaches, including, but not limited to, capability of being performed in a single reactor and/or without an intermediate isolation or purification step, does not produce dangerous products (i.e., $H_2(g)$) on a large scale, demonstrates better atom efficiency, reduced side reactions, simplified workup conditions, better yields, recycling of reaction components, and fewer waste products.

The starting materials, intermediates, and products of the various embodiments of the present disclosure may contain one or more chiral centers and/or double bonds and therefore, may exist as stereoisomers, such as double-bond isomers (i.e., geometric isomers), enantiomers, or diastereomers. The starting materials, intermediates, and products may also exist as epimers when diastereomers have the opposite stereochemical configuration at only one of two or more stereogenic centers. Accordingly, compounds within the scope of the present disclosure encompass all possible enantiomers and stereoisomers of the illustrated compounds, including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers, respectively, using separation techniques or chiral synthesis techniques known to the skilled artisan. The starting materials, intermediates, and products of the present disclosure may exist as geometric isomers. The present disclosure encompasses the various geometric isomers and mixtures thereof resulting from the position of a double bond, the arrangement of substituents around a carbon-carbon double bond, or arrangement of substituents around a carbocyclic ring. Non-hydrogen substituents around a carbon-carbon double bond may be referred to as having a "cis" or "trans" configuration, where "cis" represents substituents on the same side of the double bond and "trans" represents substituents on opposite sides of the double bond. The arrangements of substituents around a carbocyclic ring may also be designated as "cis" or "trans", where the term "cis" represents substituents on the same face of the carbocyclic ring and the term "trans" represents substituents on the opposite face of the carbocyclic ring. The terms "cis" and "trans" are common terms for representing isomeric differences in organic compounds and will be readily understood by one having ordinary skill in the art. For a more detailed discussion of ring substitution, see, Eliel and Wilen, "Sterochemistry of Organic Compounds", Wiley-Interscience, New York, 1994, pp 726-727.

In certain embodiments, the present disclosure provides for processes for converting a first isomer of a cyclic organic compound to a second isomer by one or more chemical transformations for use in the synthesis of aroma or perfume components; in particular, the epimerization of a first isomer of a cyclohexenyl alkyl ketone to a second isomer. Subsequent to the epimerization, the second isomer of the cyclohexenyl alkyl ketone may be converted to a component for a fragrance or perfume composition. The chemical transformations may be performed in situ (i.e., without isolation or purification), or with isolation of intermediate compounds. In certain embodiments, the chemical transformations may be performed in a single reactor. In specific embodiments, the chemical transformations may be performed in one step or in multiple steps. The chemical transformations may include reacting the cyclic organic compounds or intermediates with additional reagents using the epimerization/aldol condensation process described herein. Intermediates may be used with or without purification by techniques known to those skilled in the art, e.g., filtration, distillation, sublimation, crystallization, trituration, extraction, chromatography, and any combinations thereof.

According to one embodiment, the present disclosure provides a process for the epimerization of a substituted cyclohexene. The process may comprise the steps of providing to a reactor a first isomer of a cyclohexenyl alkyl ketone compound according to Formula I wherein $R^1$, $R^2$, $R^3$, $R^4$, $R^5$, $R^6$, $R^7$, and $R^8$ are described herein; and epimerizing the first isomer of the cyclohexenyl alkyl ketone with a base to form a second isomer of the cyclohexenyl alkyl ketone. According to these embodiments, epimerizing the first isomer includes deprotonating the hydrogen at the C1 carbon in the first isomer of the cyclohexenyl alkyl ketone and reprotonating the C1 carbon on the opposite face of the ring to form the second isomer of the cyclohexenyl alkyl ketone.

In certain embodiments, the cyclohexenyl alkyl ketone is a 1-(2-alkyl-3-cyclohexen-1-yl)-alkanone according to Formula I wherein $R^2$ may be an alkyl (such as $C_1$-$C_4$ alkyl). For purposes herein, all embodiments of the cyclohexenyl alkyl ketones will be referred to as 1-(2-alkyl-3-cyclohexen-1-yl)-alkanone, although one skilled in the art would understand that in other embodiments, $R^2$ may be selected from non-alkyl substituents, such as, for example, alkoxy (such as $C_1$-$C_4$ alkoxy), siloxy (—OSi(alkyl)$_3$), aromatic (e.g., phenyl) or halogen. In certain embodiments, each of $R^1$, $R^3$, $R^4$, $R^5$, $R^6$, $R^7$, and $R^8$ may be independently selected from hydrogen, alkyl (such as $C_1$-$C_4$ alkyl), alkoxy (such as $C_1$-$C_4$ alkoxy), siloxy (—OSi(alkyl)$_3$), aromatic (e.g., phenyl) or halogen. In certain embodiments, two substituents may come together to form a carbocyclic or heterocyclic 5-, 6-, or 7-membered ring. For example, any of $R^1$ and $R^2$, $R^1$ and $R^7$ or $R^8$, $R^5$ or $R^6$ and $R^7$ or $R^8$, $R^4$ and $R^5$ or $R^6$, $R^4$ and $R^3$, or $R^3$ and $R^2$ may come together to form a carbocyclic or heterocyclic 5-, 6-, or 7-membered ring. In specific embodiments, $R^1$ and $R^2$ may be each independently $C_1$-$C_4$ alkyl, and $R^3$, $R^4$, $R^5$, $R^6$, $R^7$, and $R^8$ may be each independently selected from the group consisting of H and $C_1$-$C_4$ alkyl. In one embodiment, $R^1$, $R^2$, $R^7$, and $R^8$ are methyl and $R^3$, $R^4$, $R^5$, and $R^6$ are hydrogen (i.e., the structure is 1-(2,6,6-trimethylcyclohex-3-en-1-yl)-ethanone). Other cyclic structures corresponding to the general structure of Formula I are within the subject matter of the present application, such as, for example, but not limited to, cyclohexanyl alkyl ketones (for example, where the cyclohexenyl double bond has been reduced, such as, by a hydrogenation reaction). In Formula I, the dotted bond between C3 and C4 carbons indicates that structure encompasses compounds having either a single or double bond between C3 and C4.

In certain embodiments, the 1-(2-alkyl-3-cyclohexen-1-yl)-alkanone may be a product of a Diels-Alder-type [4+2] cycloaddition reaction. A Diels-Alder-type [4+2] cycloaddition reaction describes a [4+2] cycloaddition between a diene component having a conjugated 1,3-diene functionality and a dienophile component having a reactive double bond. The diene may be any suitable cyclic and acyclic compounds having a conjugated 1,3-diene moiety that may adopt an s-cis conformation, for example, but not limited to, 1,3-pentadiene (piperylene). The dienophile may be any suitable compounds having a double carbon-carbon bond that may be reactive with a 1,3-diene, for example, in a Diels-Alder cycloaddition, such as, but not limited to, 4-methyl-3-penten-2-one (mesityl oxide). In certain embodiments, the 1-(2-alkyl-3-cyclohexen-1-yl)-alkanone may be a product of a Diels-Alder-type [4+2] cycloaddition reaction obtained via standard, well-known synthetic methodologies, see e.g. Smith and March (Eds.), March's Advanced Organic Chemistry-Reactions, Mechanisms, and Structure, Fifth Edition, 2001, John Wiley & Sons, New York at pages 1062-1075. In other embodiments, the 1-(2-alkyl-3-cyclohexen-1-yl)-alkanone may be a product of a Diels-Alder-type [4+2] cycloaddition reaction conducted in a Lewis acidic ionic liquid. Suitable non-limiting examples of Diels-Alder-type [4+2] cycloaddition reactions conducted in a Lewis acidic ionic liquid are described in detail in co-pending U.S. Provisional Application identified by "Process For Conducting An Organic Reaction In Ionic Liquids", filed on a date even with the present application and assigned to The Procter & Gamble Company, Cincinnati, Ohio. According to one embodiment, a Diels-Alder cycloaddition of piperylene and mesityl oxide may produce 1-(2,6,6-trimethylcyclohex-3-en-1-yl)-ethanone (as a mixture of cis and trans ring isomers).

In certain embodiments, the first isomer of the 1-(2-alkyl-3-cyclohexen-1-yl)-alkanone may be the kinetically favored isomer in the Diels-Alder-type [4+2] cycloaddition reaction and the second isomer may be the thermodynamically favored isomer in the Diels-Alder-type [4+2] cycloaddition reaction. As used herein, the term "kinetically favored isomer" means the product isomer that is produced at a faster rate than the other isomer(s). As used herein, the term "thermodynamically favored isomer" means the product isomer that is more thermodynamically stable than the other isomer(s). In specific embodiments in a Diels-Alder-type [4+2] cycloaddition reaction, the kinetically favored isomer may be a cis-1-(2-alkyl-3-cyclohexen-1-yl)-alkanone, such as, for example, cis-1-(2,6,6-trimethylcyclohex-3-en-1-yl)-ethanone and the thermodynamically favored isomer may be a trans-1-(2-alkyl-3-cyclohexen-1-yl)-alkanone, such as, for example, trans-1-(2,6,6-trimethylcyclohex-3-en-1-yl)-ethanone.

In certain embodiments, the process for the epimerization of a substituted cyclohexene comprises the steps of providing to a reactor a first isomer that is a cis-isomer of the 1-(2-alkyl-3-cyclohexen-1-yl)-alkanone according to Formula II and the process comprises epimerizing the cis-1-(2-alkyl-3-cyclohexen-1-yl)-alkanone to the second isomer of the 1-(2-alkyl-3-cyclohexen-1-yl)-alkanone, where the second isomer is a trans-isomer of the 1-(2-alkyl-3-cyclohexen-1-yl)-alkanone according to Formula III, wherein $R^1$, $R^2$, $R^3$, $R^4$, $R^5$, $R^6$, $R^7$, and $R^8$ are described herein.

II

III

Referring to Formulas II and III, $R^2$ and the carbonyl substituent are on the same side (i.e., cis) or opposite side (i.e., trans) of the plane of the cyclohexene ring, respectively. In specific embodiments, the first isomer may be cis-1-(2,6,6-trimethylcyclohex-3-en-1-yl)-ethanone and the second isomer may be trans-1-(2,6,6-trimethylcyclohex-3-en-1-yl)-ethanone.

Other cyclic structures corresponding to the general structure of Formulas II and/or III are within the subject matter of the present application.

In certain embodiments, the process for the epimerization of a substituted cyclohexene comprises the steps of providing to a reactor a mixture of substituted cyclohexene isomers, such as, a mixture of stereoisomers, enantiomers, diastereomers, and/or epimers having a general structure according to Formula I. In specific embodiments, the mixture of substituted cyclohexene isomers comprises a mixture of cis-1-(2-alkyl-3-cyclohexen-1-yl)-alkanone and trans-1-(2-alkyl-3-cyclohexen-1-yl)-alkanone. In certain embodiments, the mixture of substituted cyclohexene isomers comprises more cis-1-(2-alkyl-3-cyclohexen-1-yl)-alkanone than trans-1-(2-alkyl-3-cyclohexen-1-yl)-alkanone. For example, in certain embodiments, the cis:trans ratio of the 1-(2-alkyl-3-cyclohexen-1-yl)-alkanone may be greater than 10:1. According to these embodiments, epimerizing the first isomer of the 1-(2-alkyl-3-cyclohexen-1-yl)-alkanone to the second isomer of the 1-(2-alkyl-3-cyclohexen-1-yl)-alkanone results in conversion of the cis isomer in the mixture of stereoisomers into the trans isomer of 1-(2-alkyl-3-cyclohexen-1-yl)-alkanone. As a result, a majority, and in certain embodiments, substantially all of the 1-(2-alkyl-3-cyclohexen-1-yl)-alkanone in the product is trans-1-(2-alkyl-3-cyclohexen-1-yl)-alkanone. As used herein, the term "majority" means greater than 50% and the term "substantially all" means greater than 90%.

In certain embodiments, the epimerizing the first isomer of the 1-(2-alkyl-3-cyclohexen-1-yl)-alkanone may comprise contacting the cyclohexenyl alkyl ketone with a base, such as basic alkali and/or alkaline metal compounds, for example, an alkali metal amide (for example, but not limited to, sodium amide ($NaNH_2$) or lithium amide ($LiNH_2$)), a metal alkoxide (for example, but not limited to, sodium methoxide (NaOMe), lithium methoxide (LiOMe), potassium methoxide (KOMe), sodium ethoxide (NaOEt), lithium ethoxide (LiOEt), potassium ethoxide (KOEt), lithium tert-butoxide (LiOt-Bu), potassium tert-butoxide (KOt-Bu), potassium isobutoxide (KOi-Bu), sodium isopropoxide (NaOi-Pr), potassium isopropoxide (KOi-Pr), titanium tetra-n-butoxide ($Ti(On-Bu)_4$), titanium tetraisopropoxide ($Ti(OiPr)_4$)), an alkali metal carbonate (for example, but not limited to, sodium carbonate ($Na_2CO_3$) or potassium carbonate ($K_2CO_3$)), an alkali metal hydrogen carbonate (for example, but not limited to, sodium hydrogen carbonate ($NaHCO_3$) or potassium hydrogen carbonate ($KHCO_3$)) or mixtures of any thereof to form the second isomer of 1-(2-alkyl-3-cyclohexen-1-yl)-alkanone (i.e., the trans-isomer). In certain embodiments, the first isomer may be epimerized with a metal alkoxide base such as a metal alkoxide selected from the group consisting of potassium tert-butoxide, lithium tert-butoxide, sodium methoxide, titanium tetra-n-butoxide, titanium tetraisopropoxide, and mixtures of any thereof. In specific embodiments, the metal alkoxide base may be potassium tert-butoxide. Other bases may also be suitable for epimerizing the cis- to the trans-1-(2,6,6-trimethylcyclohex-3-en-1-yl)ethanone and are within the scope of this disclosure. As disclosed herein, epimerizing the first isomer of the 1-(2-alkyl-3-cyclohexen-1-yl)-alkanone with a base to for the second isomer may comprise epimerizing the kinetically favored isomer from a Diels-Alder cycloaddition reaction to a thermodynamically favored isomer.

In certain embodiments of the process for epimerization of a cyclohexene according to the present disclosure, the molar ratio of substituted cyclohexene to metal alkoxide base may range from about 0.25:1.0 to about 1.50:1.0, and in other embodiments from about 0.50:1.0 to about 1.10:1.0, and in still other embodiments from about 0.55:1.0 to about 0.75:1.0. In specific embodiments, the molar ratio of the mixture of cis/trans-1-(2-alkyl-3-cyclohexen-1-yl)-alkanone isomers to KOt-Bu may range from about 0.25:1.0 to about 1.50:1.0, and in other embodiments from about 0.50:1.0 to about 1.10:1.0, and in still other embodiments from about 0.55:1.0 to about 0.75:1.0.

In certain embodiments, the epimerization of a cyclohexene of the present disclosure comprises the step of contacting the 1-(2-alkyl-3-cyclohexen-1-yl)-alkanone with a mixture of metal alkoxide bases. According to certain embodiments, the mixture of metal alkoxide bases may comprise potassium tert-butoxide and titanium tetra-n-butoxide in a ratio ranging from 0.25:1.0 to 2:1, in other embodiments from 0.5:1.0 to 2:1 and in specific embodiments from 1:1 to 2:1. According to these embodiments, each metal alkoxide base may have an independent molar ratio of substituted cyclohexene to metal alkoxide base ranging from about 0.25:1.0 to about 1.50:1.0, and in other embodiments from about 0.50:1.0 to about 1.10:1.0, and in still other embodiments from about 0.55:1.0 to about 0.75:1.0. In specific embodiments, a mixture of metal alkoxide bases comprising KOt-Bu and Ti(On-Bu)$_4$ may be used to epimerize a first isomer of 1-(2-alkyl-3-cyclohexen-1-yl)-alkanone to a second isomer in which the molar ratio of the mixture of cis/trans-1-(2-alkyl-3-cyclohexen-1-yl)-alkanone isomers to KOt-Bu may range from about 0.25:1.0 to about 1.50:1.0, and in other embodiments from about 0.50:1.0 to about 1.10:1.0, and in still other embodiments from about 0.55:1.0 to about 0.75:1.0, and the molar ratio of the mixture of cis/trans-1-(2-alkyl-3-cyclohexen-1-yl)-alkanone isomers to Ti(On-Bu)$_4$ may range from about 0.25:1.0 to about 1.50:1.0, and in other embodiments from about 0.50:1.0 to about 1.10:1.0, and in still other embodiments from about 0.55:1.0 to about 0.75:1.0.

The atom efficiency, atom utilization, or atom economy evaluates the amount of waste generated by alternative routes to a specific product. The atom efficiency may be calculated by dividing the molecular weight of the desired product by the sum total of the molecular weights of all chemical components produced in the stoichiometric equation for the reactions involved. The comparison is made on a theoretical basis, i.e., 100% chemical yield. Therefore, in certain embodiments, the atom efficiency of the epimerization process using one metal alkoxide base may be greater than the atom efficiency of the epimerization process using more than one metal alkoxide base.

Epimerizing the first (cis) isomer of the 1-(2-alkyl-3-cyclohexen-1-yl)-alkanone to the second (trans) isomer of the 1-(2-alkyl-3-cyclohexen-1-yl)-alkanone may be done in any suitable inert organic solvent, such as, for example, diethyl ether, tetrahydrofuran, and alcohol solvents, such as methanol, ethanol, and n-, sec-, iso- or tert-butanol. Epimerizing may comprise contacting the first isomer with a metal alkoxide base, such as, for example, potassium tert-butoxide in an organic solvent at a temperature ranging from 0° C. to 100° C. and in certain embodiments from 25° C. to 66° C. As will be discussed further herein, the epimerized product (i.e., the trans-1-(2-alkyl-3-cyclohexen-1-yl)-alkanone) may be directly submitted to an aldol condensation process, for example, in a single reactor process.

Aldol Condensation Process

The aldol condensation reaction is the acid- or base-catalyzed condensation of an aldehyde or ketone with a second aldehyde or ketone. In an aldol condensation reaction, the enolate of an aldehyde or a ketone adds to the carbonyl carbon of another aldehyde or ketone to form an aldol addition product. Under certain conditions, the aldol addition product may undergo further transformations, e.g., dehydration to from an aldol condensation product. In certain embodiments, the dehydration occurs spontaneously or may be performed in another step.

According to certain embodiments of the present disclosure, the second isomer of the 1-(2-alkyl-3-cyclohexen-1-yl)-alkanone may be converted to a composition suitable for use as a fragrance enhancement compound. For example, the second isomer may be converted by an aldol condensation process with an aldehyde or ketone to produce a fragrance component. In specific embodiments, the second isomer may be converted to 6-damascone via an aldol condensation.

According to specific embodiments of the present disclosure, the process for epimerization of a cyclohexene, as described herein, may further comprise condensing the second isomer of the 1-(2-alkyl-3-cyclohexen-1-yl)-alkanone with an aldehyde followed by elimination of water to form a first aldol condensation product. In these embodiments, the condensing reaction is an aldol condensation reaction. According to these embodiments, the first aldol condensation product may be an unsaturated ketone, such as an α,β-unsaturated ketone. In specific embodiments, condensing the second isomer with an aldehyde may comprise condensing trans-1-(2,6,6-trimethylcyclohex-3-en-1-yl)-ethanone with an aldehyde followed by an elimination of water to form an aldol condensation product. For example, in one particular embodiment where the second isomer comprises trans-1-(2,6,6-trimethylcyclohex-3-en-1-yl)-ethanone, the aldehyde may be acetaldehyde (ethanal) and the aldol condensation product may be (±)-δ-damascone.

As discussed herein, according to certain embodiments, the aldol condensation may be performed in the same reactor (i.e., single reactor process) as the epimerization step. According to these embodiments, the epimerization product (i.e., trans-1-(2-alkyl-3-cyclohexen-1-yl)-alkanone) may be directly submitted to the aldol condensation conditions. For example, since certain embodiments of the epimerization process of the present disclosure utilizes a metal alkoxide base to catalyze the epimerization, that base may also be used to deprotonate the trans-1-(2-alkyl-3-cyclohexen-1-yl)-alkanone to form an enolate of the ketone. In certain embodiments, additional base may be added to the reaction medium. Addition of a second aldehyde or ketone may then result in an aldol condensation between the enolate of the trans-1-(2-alkyl-3-cyclohexen-1-yl)-alkanone and the second aldehyde or ketone as shown in equation 1. In other embodiments, the epimerization product may be isolated (i.e., worked up) prior to deprotonation with a base (i.e., a metal alkoxide base) and condensation with an aldehyde or ketone in an aldol condensation.

eq. 1

(2,6,6-trimethylcyclohex-3-en-1-yl)but-3-en-1-one to (E)-trans-1-(2,6,6-trimethylcyclohex-3-en-1-yl)but-2-en-1-one (i.e., (±)-δ-damascone) is shown in equation 2.

The elimination of water during the aldol condensation forms an unsaturated ketone, as discussed herein. The dehydration step can occur spontaneously during the aldol reaction or in a separate step. In certain embodiments, the elimination of water may occur under the reaction conditions to produce the unsaturated ketone. In other embodiments, the dehydration reaction can be conducted by exposing the reactants to air or vacuum at a temperature ranging from about 10° C. to about 30° C. In still other embodiments, the elimination of water may occur under acid catalysis. Suitable acid catalysts include, but are not limited to, organic acids, Lewis acids, and inorganic acids. Organic acids include, carboxylic acids (such as, for examples, acetic acid) and sulfonic acids (such as, for example, p-toluenesulfonic acid). Lewis acids include, but are not limited to, many common Lewis acids and may also include Lewis acidic ionic liquids. Inorganic acids include, but are not limited to, hydrochloric acid, sulfuric acid, nitric acid and the like In other embodiments, the elimination of water may produce a mixture of a first aldol condensation product and a second aldol condensation product. According to these embodiments, the first aldol condensation product may be an α,β-unsaturated ketone and the second aldol condensation product may be a constitutional isomer of the first aldol condensation product, for example, an unconjugated unsaturated ketone, such as a β,γ-unsaturated ketone. In these embodiments, the process for epimerization of the cyclohexene may further comprise isomerizing the second aldol condensation product to the first aldol condensation product. For example, the process may further comprise isomerizing the β,γ-unsaturated ketone to the α,β-unsaturated ketone. In certain embodiments, the isomerization may occur spontaneously during the quenching and/or workup conditions. For example, the aldol condensation reaction may be quenched or worked up with a mild acid which may also catalyze the isomerization of the second aldol condensation product to the first aldol condensation product. Alternatively, the isomerization may require a separate chemical step, such as treating the second aldol condensation product with an isomerization catalyst to isomerize it to the first aldol condensation product. In specific embodiments, the second aldol condensation product may be trans-1-(2,6,6-trimethylcyclohex-3-en-1-yl)but-3-en-1-one and the first aldol condensation product may be (E)-trans-1-(2,6,6-trimethylcyclohex-3-en-1-yl)but-2-en-1-one (i.e., (±)-δ-damascone). The isomerization of trans-1-

The present disclosure also relates to processes for converting a first isomer of an 1-(2-alkyl-3-cyclohexen-1-yl)-alkanone to a first aldol condensation product by a sequence of chemical transformations, and in particular, the epimerization of the first isomer of 1-(2-alkyl-3-cyclohexen-1-yl)-alkanone to the second isomer of the 1-(2-alkyl-3-cyclohexen-1-yl)-alkanone (for example, with a metal alkoxide base) and the aldol condensation of a second isomer of a cyclohexenyl methyl ketone to an aldol condensation product. The chemical transformations may be performed in situ, or with isolation of intermediate compounds. In certain embodiments, the chemical transformations may be performed in a single reactor. That is, the epimerizing step and the condensing step (i.e., the aldol condensation) may be performed in a single reactor. The chemical transformations may be performed in one step, such as by the sequential addition of reagents to the reactor, or in multiple steps (i.e., with isolation or work-up steps between chemical transformations). Intermediates may be used with or without purification by techniques known to those in the art, e.g., filtration, distillation, sublimation, crystallization, trituration, extraction, and chromatography. As will be understood by those having ordinary skill in the art, elimination or work-up or isolation steps, for example by performing multiple chemical transformations in a single reactor, may increase the overall efficiency and yield of a chemical process, for example, by reducing material lost as a result of a work-up, isolation, or purification procedure, and may generally result in greater economic efficiency, for example, by decreased process time, decreased reactor requirements (one reactor instead of multiple reactors), eliminated work-up chemical expenses (such as, but not limited to, solvent and workup reagent purchase costs and disposal/recycling costs) and eliminated purification requirements (time, purchase costs and disposal/recycling costs).

According to another embodiment, the present disclosure relates to processes for converting a first isomer of a 1-(2-alkyl-3-cyclohexen-1-yl)-alkanone to an aldol condensation product for use as aroma or perfume ingredients. In certain embodiments, the present disclosure provides a process for producing an aldol condensation product comprising the steps of epimerizing a first isomer of a cyclohexenyl alkyl ketone according to Formula I:

wherein $R^1$, $R^2$, $R^3$, $R^4$, $R^5$, $R^6$, $R^7$, and $R^8$ are described herein, with a base to form a second isomer of an alkyl cyclohexenyl ketone; and condensing the second isomer with an aldehyde followed by elimination of water to form a first aldol condensation product.

In certain embodiments, the present disclosure provides for a process for producing an aldol condensation product comprising the steps of epimerizing a first cis/trans isomer of a 1-(2-alkyl-3-cyclohexen-1-yl)-alkanone according to Formula I, wherein $R^1$, $R^2$, $R^3$, $R^4$, $R^5$, $R^6$, $R^7$, and $R^8$ are described herein, with a metal alkoxide base, such as potassium tert-butoxide, to form a second cis/trans isomer of the 1-(2-alkyl-3-cyclohexen-1-yl)-alkanone; and condensing the second isomer of the 1-(2-alkyl-3-cyclohexen-1-yl)-alkanone with an aldehyde followed by elimination of water to form a first aldol condensation product. In specific embodiments, the first cis/trans isomer of the 1-(2-alkyl-3-cyclohexen-1-yl)-alkanone is a 1,2-cis ring isomer of the 1-(2-alkyl-3-cyclohexen-1-yl)-alkanone and the second cis/trans isomer of the 1-(2-alkyl-3-cyclohexen-1-yl)-alkanone is a 1,2-trans ring isomer of the 1-(2-alkyl-3-cyclohexen-1-yl)-alkanone.

In certain embodiments first cis/trans isomer of a 1-(2-alkyl-3-cyclohexen-1-yl)-alkanone may be a product of a Diels-Alder-type [4+2] cycloaddition reaction. In specific embodiments, the Diels-Alder-type [4+2] cycloaddition reaction may be between the dienophile, mesityl oxide, and the 1,3-diene, piperylene, that produces a mixture of the first cis/trans isomer cis-1-(2,6,6-trimethylcyclohex-3-en-1-yl)-ethanone and the second cis/trans isomer is trans-1-(2,6,6-trimethylcyclohex-3-en-1-yl)-ethanone. For example, in certain embodiments, the Diels-Alder-type cycloaddition may produce a mixture of cis- and trans-1-(2,6,6-trimethylcyclohex-3-en-1-yl)-ethanone, wherein the cis isomer predominates.

In certain embodiments, the base comprises a metal alkoxide base, such as basic alkali and alkaline metal compounds. In certain embodiments, the metal alkoxide base comprises an alkali metal alkoxide, such as, but not limited to, sodium methoxide (NaOMe), lithium methoxide (LiOMe), potassium methoxide (KOMe), sodium ethoxide (NaOEt), lithium ethoxide (LiOEt), potassium ethoxide (KOEt), lithium tert-butoxide (LiOt-Bu), potassium tert-butoxide (KOt-Bu), potassium isobutoxide (KOi-Bu), sodium isopropoxide (NaOi-Pr), potassium isopropoxide (KOi-Pr), titanium tetra-n-butoxide (Ti(On-Bu)$_4$), titanium tetraisopropoxide (Ti(O-iPr)$_4$) or any mixtures thereof. In specific embodiments, the metal alkoxide base may be selected from the group consisting of potassium tert-butoxide, lithium tert-butoxide, sodium methoxide, titanium tetra-n-butoxide, titanium tetra-iso-propoxide, and mixtures of any thereof and in particular embodiments; the metal alkoxide base is potassium tert-butoxide. Suitable solvents for the aldol condensation step of the process may be the same as those inert organic solvents discussed herein for the epimerization step, for example, ethereal solvents (diethyl ether, and tetrahydrofuran).

In certain embodiments, the aldehyde may be selected from linear, branched, or cyclic $C_2$-$C_{12}$ aliphatic aldehydes. Other aldehydes and ketones known in the art may also be suitable for adding to the carbonyl carbon of the cyclohexenyl alkyl ketones described herein to form an aldol addition product and are within the scope of this disclosure. In specific embodiments, the aldehyde is ethanal (acetaldehyde).

In certain embodiments of the process for producing an aldol condensation product where the second cis/trans isomer is trans-1-(2,6,6-trimethylcyclohex-3-en-1-yl)ethanone, the aldehyde may be acetaldehyde. According to these embodiments, the first aldol condensation product is (±)-δ-damascone. As discussed herein, in particular embodiments the epimerizing step and the condensing step may be performed in a single reactor, for example, without an intermediate work-up, isolation, or purification step between the epimerization step and the condensation step.

In other embodiments, the condensing step for the trans-1-(2,6,6-trimethylcyclohex-3-en-1-yl)ethanone or other 1-(2-alkyl-3-cyclohexen-1-yl)-alkanone may also be performed with another aldehyde or ketone reagent to form a condensation product that may be useful as a fragrance component. In these embodiments, the condensation products (i.e., aldol reaction, and optionally the elimination reaction) will be other cyclohexene products of interest, such as cyclohexene products with different aromas. The processes may further comprise purifying the condensation product, for example, by a purification method selected from crystallization, distillation or chromatography. Suitable examples of these purification methods are described herein in reference to purifying the product of the epimerization process.

Certain embodiments of the aldol condensation process according to the present disclosure are illustrated in equation 1. Referring to equation 1, to a trans-1-(2-alkyl-3-cyclohexen-1-yl)-alkanone isomer of Formula I is added an excess (such as about 1 to 20 equivalents) of a metal alkoxide base, for example, potassium tert-butoxide and an aldehyde comprising acetaldehyde (about 1 to 10 equivalents) in an inert organic solvent, such as tetrahydrofuran. The reaction vessel may be held at a reaction temperature ranging from about 0° C. to 50° C., and in certain embodiments from 10° C. to 30° C. or even from 15° C. to about 20° C. The product, such as (±)-δ-damascone, may be isolated at about 80% to about 100% yield, and optionally purified. In certain embodiments, the reagents (i.e., base and aldehyde) may be added slowly to the reaction mixture at a rate such that side reactions and self condensation of reactants is minimized. One skilled in the art will understand that the addition rate may vary according to reaction size.

Single Reactor Process

According to various embodiments, the epimerization and aldol condensation processes described herein may be performed in a single reactor. As used herein, the phrase "single reactor" means that two or more chemical transformations are performed in one or more reactors without intermediate isolation, workup, or quenching steps. For example, according to these embodiments, the mixture or cis- and trans-1-(2,6,6-trimethylcyclohex-3-en-1-yl)-ethanone may be submitted to epimerization conditions and once the epimerization is substantially complete, the reaction solution comprising substantially all trans-1-(2,6,6-trimethylcyclohex-3-en-1-yl)-ethanone may be subjected directly to the aldol condensation conditions by adding the aldehyde to the epimerization product.

In certain embodiments, the present disclosure provides for a single reactor process for the production of a cyclohexene product comprising the steps of epimerizing a 1,2-cis-isomer of a 1-(2-alkyl-3-cyclohexen-1-yl)-alkanone with a metal alkoxide base, such as, potassium tert-butoxide, to form a 1,2-trans-isomer of the 1-(2-alkyl-3-cyclohexen-1-yl)-alkanone; and condensing the 1,2-trans-isomer of the 1-(2-alkyl-3-cyclohexen-1-yl)-alkanone with an aldehyde followed by elimination of water to form a first aldol condensation product, wherein the epimerizing step and the condensing step are performed in a single reactor. As discussed herein, in certain embodiments, the reactant for the epimerization step may be a mixture of the 1,2-cis-isomer of a 1-(2-alkyl-3-cyclohexen-1-yl)-alkanone and the 1,2-trans-isomer of a 1-(2-alkyl-3-cyclohexen-1-yl)-alkanone. In specific embodiments, the 1,2-cis-isomer of the 1-(2-alkyl-3-cyclohexen-1-yl)-alkanone is cis-1-(2,6,6-trimethylcyclohex-3-en-1-yl)-ethanone, the 1,2-trans-isomer of the 1-(2-alkyl-3-cyclohexen-1-yl)-alkanone is trans-1-(2,6,6-trimethylcyclohex-3-en-1-yl)-ethanone.

Figure 1:
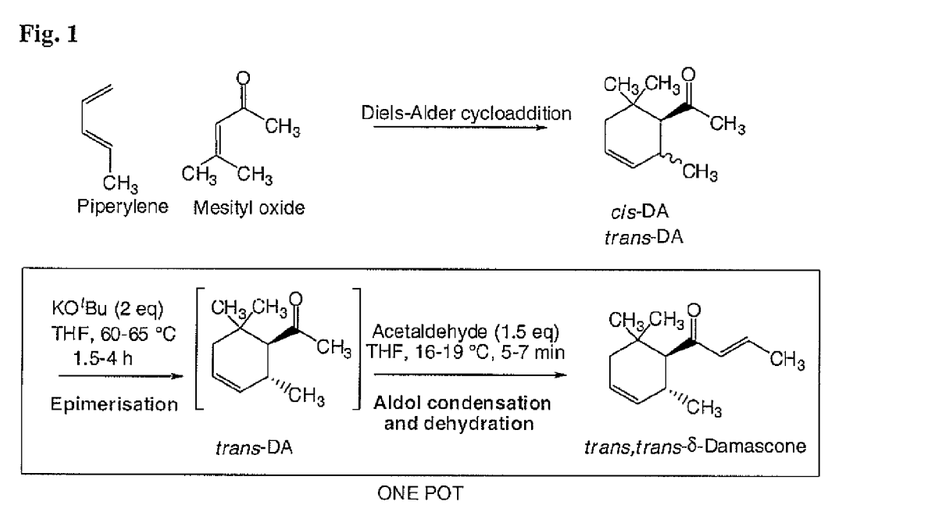
FIG. 1 illustrates a Diels-Alder cycloaddition and a single reactor approach involving an epimerization and aldol condensation to synthesize δ-damascone from the Diels-Alder cycloadduct.

As discussed herein, in certain embodiments, where the 1,2-trans-isomer of the 1-(2-alkyl-3-cyclohexen-1-yl)-alkanone is trans-1-(2,6,6-trimethylcyclohex-3-en-1-yl)-ethanone, the aldehyde in the aldol condensation process may be acetaldehyde such that the product of the single reactor process is (E)-trans-1-(2,6,6-trimethylcyclohex-3-en-1-yl)but-2-en-1-one (i.e., (±)-δ-damascone). As discussed herein, in certain embodiments, the aldol condensation reaction may result in a mixture of a first aldol condensation product and a second aldol condensation product, as described in detail herein, wherein the process may further comprise isomerizing the second aldol condensation product to the first aldol condensation product. In specific embodiments, the 1,2-cis-isomer of the 1-(2-alkyl-3-cyclohexen-1-yl)-alkanone may the product of a Lewis acid catalyzed Diels-Alder-type [4+2] cycloaddition reaction in a Lewis acidic ionic liquid, such as those reactions and processes described in co-pending U.S. Provisional Application identified by "Process For Conducting An Organic Reaction In Ionic Liquids", filed on a date even with the present application and assigned to The Procter & Gamble Company, Cincinnati, Ohio. This approach to (±)-δ-damascone is illustrated schematically in FIG. 1.

In certain embodiments, the single reactor process may further comprise purifying the first aldol condensation product. The isolation and purification of the first aldol condensation product may be effected, if desired, by any suitable separation or purification procedure, such as those known in the art, for example, distillation, filtration, extraction, crystallization, and chromatography, or a combination of these procedures. In specific embodiments, the first aldol condensation product may be purified by distillation, such as, but not limited to, simple distillation, fractional distillation, reduced pressure distillation, vacuum distillation, steam distillation, azeotropic distillation, Kugelrohr distillation, or other distillation technique. Other equivalent separation or isolation procedures known in the art may also be used.

In certain embodiments, the first aldol condensation product may have use as a component of scents, perfumes, fragrances, and air fresheners. In specific embodiments of the various processes described throughout the present disclosure, the first aldol condensation product may be (±)-δ-damascone, and in other embodiments, the first aldol condensation product is (±)-δ-damascone having greater than 82% by weight of the trans-ring isomer. In other embodiments the first aldol condensation product is (±)-δ-damascone having greater than 85% by weight of the trans-ring isomer, or in certain embodiments greater than 90% by weight of the trans-ring isomer, or even greater than 95% by weight of the trans-ring isomer.

Performing the epimerization and aldol condensation processes in a single reactor may provide certain advantages over other synthetic approaches to these compounds, including, but not limited to, increased atom efficiency; eliminating additional process steps, such as extraction steps after the epimerization process; eliminating drying steps during the aldol condensation process; reducing the volumes of organic solvents, reagents, and water necessary for the transformations; eliminating the formation of solid potassium hydroxide or other dangerous side products; and improved opportunities for recycling starting materials, products and by-products from the reaction mixture, such as solvents, reactants, and by-products by separation techniques, for example, distillation.

According to certain embodiments, the processes described herein may comprise a single reactor epimerization/aldol condensation-elimination protocol according to the present disclosure. In one embodiment of the single reactor process, a single extraction protocol after the aldol condensation-elimination step may comprise the steps of subjecting the organic phase from the extraction to fractional distillation to provide purified (±)-δ-damascone. In another embodiment of the single reactor process, the extraction step may be eliminated and a simple phase separation protocol may be used instead. In this embodiment, the organic phase from the phase separation may be subjected to fractional distillation to provide purified (±)-δ-damascone. In yet another embodiment of the single reactor process, the aqueous work-up after the aldol condensation-elimination step may be eliminated and the product mixture may be subjected directly to fractional distillation to provide purified (±)-δ-damascone. Certain embodiments of the single reactor process may provide advantages over the prior art three separate reaction approach since at least one and in certain embodiments, numerous work-up and/or purification steps are eliminated, thereby reducing processing steps, infrastructure requirements, byproduct production and disposal requirements and overall increased yields of product.

INDUSTRIAL APPLICATION

The various embodiments of the epimerization and aldol condensation processes of the present disclosure may be used to provide useful industrial products, such as scents, fragrance components, and perfumes. The epimerization and aldol condensation process of the present disclosure may be readily scaled-up for industrial applications to be carried out in a plant that includes reactor types known in the art. Examples of such reactors include, but are not limited to, batch reactors, semi-batch reactors, and continuous reactors. The plant may include, in combination, a) at least one stirred reactor system, b) at least one inlet line into a first reactor system for the substituted cyclohexene and the catalyst system, and c) at least one separator to separate the desired aldol condensation products, which may optionally include a recycle loop for solvents and/or reactants and/or products. In certain embodiments, since the processes according to the present disclosure may be performed in a single reactor, various economic advantages may be realized by reducing the industrial infrastructure, such as the number of reactors, necessary for the production of the fragrance components described herein.

Unless specified otherwise, the reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The processes of the present disclosure may be carried out at within a temperature range from −10° C. to 200° C., and in certain embodiments in the range of 15° C. to 150° C., and in other embodiments in the range of 25° C. to 66° C.

The processes of the present disclosure may be carried out in a proper amount of any solvent as long as it does not adversely affect to the reaction. Many standard organic or inorganic solvents may be suitable for use in the processes described herein, however, the solvents used in the reaction may affect the yield of the reaction and stereoselectivity of the reaction products. Typically, solvents may comprise from about 50% to about 95% by weight of the reaction mixture. Suitable solvents include ionic, polar or non-polar; organic or inorganic solvents, for example, but not limited to, aromatic solvents, such as, but not limited to toluene and benzene (including halogenated benzene solvents); ethereal solvents, such as, but not limited to, diethyl ether and tetrahydrofuran (THF); halogenated solvents, such as, but not limited to, dichloromethane; and water. In other embodiments, the reactions may be performed neat.

The individual reagents described herein may be combined simultaneously or sequentially in any order, and in the presence or absence of a solvent. The components of the catalysts may also be added separately and at different temperatures to allow for selective and controlled contact between the components. The reagents, solvents, or mixtures thereof may be introduced into the processes in a continuous or batch fashion.

Isolation and purification of the reagents, intermediates and products described herein may be effected, if desired, by any suitable separation or purification procedure such as, for example, filtration, distillation, sublimation, crystallization, trituration, extraction, and chromatography, or a combination of these procedures. However, other equivalent separation or isolation procedures can also be used. According to certain embodiments, any conventional method of purification may be used. For example, in those embodiments where the product is a solid, it may be purified, for example, by crystallization or recrystallization. Crystallization or recrystallization using a single solvent or mixed solvent system are contemplated. In those embodiments, where the product is a liquid or a low melting solid, it may be purified using a distillation method, such as, but not limited to simple distillation, steam distillation, fractional distillation, azeotropic distillation, spinning band distillation, vacuum or reduced pressure distillation, and combination of these methods (for example, vacuum fractional distillation). In still other embodiments, the product may be purified by chromatographic methods, such as, but not limited to column chromatography, liquid chromatography, flash chromatography, medium pressure liquid chromatography, high performance liquid chromatography (HPLC), thin layer chromatography, reverse-phase chromatography, and combinations of these methods. Alternatively, the product may be purified by using a combination of any of the above referenced purification methods.

Any starting material, intermediate, or product may occur as a stereoisomer mixture having at least about 60% (e.g., at least about 70%, at least about 75%, at least about 80%, at least about 85%, at least about 90%, at least about 95%, at least about 99%, greater than about 99%) of one of the two possible stereoisomers (cis/trans isomers). The starting materials, intermediates, and products may be substantially free of their enantiomers and the other possible stereoisomers as well as other non-stereoisomer-related materials, e.g., solvents, reagents, reaction by-products, and the like.

As described herein, the various embodiments of the processes of the present disclosure may be utilized to synthesize (±)-δ-damascone having a high degree of purity (i.e., greater than 82% by weight of the trans-ring isomer). Various embodiments of the present disclosure provide for perfume compositions comprising (±)-δ-damascone produced by the processes described herein. For example, in one embodiment, the present disclosure provides for a perfume composition comprising (±)-δ-damascone having greater than 82% by weight of the trans-ring isomer. According to these embodiments, the perfume compositions comprising the (±)-δ-damascone produced by the present processes may be utilized in a variety of commercial products. One embodiment provides for a detergent composition comprising a perfume composition comprising (±)-δ-damascone produced by the processes described herein. Another embodiment provides for a fine fragrance composition comprising the (±)-δ-damascone produced by the processes described herein. Still another embodiment provides for an air freshener composition comprising the (±)-δ-damascone produced by the processes described herein. Other commercial products requiring a specific fragrance composition that may be synthesized according to the processes described herein are also contemplated.

While various specific embodiments have been described in detail herein, the present disclosure is intended to cover various different combinations of the disclosed embodiments and is not limited to those specific embodiments described herein. The various embodiments of the present disclosure may be better understood when read in conjunction with the following representative examples. The following representative examples are included for purposes of illustration and not limitation.

EXAMPLES

Example 1

Epimerization of a Diels-Alder Cycloadduct

In this example, a mixture consisting of cis-1-(2,6,6-trimethylcyclohex-3-en-1-yl)-ethanone to trans-1-(2,6,6-trimethylcyclohex-3-en-1-yl)-ethanone is epimerized to give increased content of the trans isomer. The base is varied to determine the optimum reaction conditions.

Sample Procedure—The mixture consisting of cis-1-(2,6,6-trimethylcyclohex-3-en-1-yl)-ethanone and trans-1-(2,6,6-trimethylcyclohex-3-en-1-yl)-ethanone produced by a Diels-Alder cycloaddition (1 eq., 10 mmol, 1.67 g) is added under $N_2$ atmosphere to a suspension of base KOt-Bu (2 eq., 20 mmol, 2.24 g) and/or Ti(On-Bu)$_4$ (2 eq., 20 mmol, 2.84 g) in 10 mL tetrahydrofuran (THF) at room temperature (16° C. to 20° C.). The mixture is heated to 60° C. to 66° C. and stirred for 1.5 to 5 h to epimerize the cis-1-(2,6,6-trimethylcyclohex-3-en-1-yl)-ethanone to trans-1-(2,6,6-trimethylcyclohex-3-en-1-yl)-ethanone (as the enolate).

Different base protocols are examined. A base mixture in THF according to Table 1 is prepared and the isomeric mixture of cis- and trans-1-(2,6,6-trimethylcyclohex-3-en-1-yl)-ethanone is added to the suspension. Upon workup, the trans-cis isomeric ration is determined. A summary of the molar ratio of certain components of the epimerization process for the epimerization of 1-(2,6,6-trimethylcyclohex-3-en-1-yl)-ethanone according to certain embodiments of the present disclosure as described herein is provided in Table 1.

TABLE 1

Epimerization of 1-(2,6,6-trimethylcyclohex-3-en-1-yl)-ethanone

| Entry | DA:KOt-Bu | DA:Ti(On-Bu)$_4$ | KOt-Bu:Ti(On-Bu)$_4$ | trans:cis in product | % trans product |
|---|---|---|---|---|---|
| 1 | 1.10:1.00 | 1.10:1.00 | 1.00:1.00 | 0.82:1.00 | 45 |
| 2 | 0.77:1.00 | 0.77:1.00 | 1.00:1.00 | 5.84:1.00 | 85 |
| 3 | 0.55:1.00 | 0.55:1.00 | 1.00:1.00 | 8.82:1.00 | 90 |
| 4 | 0.73:1.00 | — | — | 13.69:1.00 | 93 |
| 5 | 0.55:1.00 | — | — | 18.56:1.00 | 95 |
| 6 | 0.73:1.00 | 1.10:1.00 | 1.50:1.00 | 25.42:1.00 | 96 |
| 7 | 0.55:1.00 | 1.10:1.00 | 2.00:1.00 | 28.14:1.00 | 97 |
| 8 | 0.55:1.00 (NaOMe) | — | — | 2.07:1.00 | 67 |

DA = Diels-Alder cycloadduct

Example 2

One-Pot Epimerization and Aldol Condensation of a Diels-Alder Cycloadduct

In this example, a substituted cyclohexene product comprising predominately (±)-δ-damascone is formed. A mixture consisting of cis-1-(2,6,6-trimethylcyclohex-3-en-1-yl)-ethanone and trans-1-(2,6,6-trimethylcyclohex-3-en-1-yl)-ethanone is epimerized and then subjected to aldol condensation conditions with acetaldehyde to produce the (±)-δ-damascone.

The mixture consisting of cis-1-(2,6,6-trimethylcyclohex-3-en-1-yl)-ethanone and trans-1-(2,6,6-trimethylcyclohex-3-en-1-yl)-ethanone produced by a Diels-Alder cycloaddition (1 eq., 10 mmol, 1.67 g) is added under N$_2$ atmosphere to a suspension of KOt-Bu (2 eq., 20 mmol, 2.24 g) in 10 mL tetrahydrofuran (THF) at room temperature (16° C. to 20° C.). The mixture is heated to 60° C. to 66° C. and stirred for 1.5 to 5 h to epimerize the cis-1-(2,6,6-trimethylcyclohex-3-en-1-yl)-ethanone to trans-1-(2,6,6-trimethylcyclohex-3-en-1-yl)-ethanone (as the enolate). The mixture is cooled to room temperature (16° C. to 19° C.) and diluted with an additional 15 mL of THF. Acetaldehyde (1.5 eq., 15 mmol, 0.83 mL) is added slowly to the mixture over 5 min with stirring. Anhydrous acetic acid (1.1 eq. to KOt-Bu, 22 mmol, 1.26 mL) is added to the mixture. The formed potassium acetate precipitate is removed by filtration, and the remaining liquid is evaporated to remove the THF solvent and the formed tert-butanol. The residue is vacuum distilled (0.066-0.27 mbar, 55° C. to 80° C. using a Kugelrohr distillation apparatus) to give the desired (±)-δ-damascone in 65.3% (calibrated GC yield after recycling of the unreacted starting material).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Disclosure are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for epimerization of a cyclohexene comprising:

providing to a reactor a first isomer of a 1-(2-alkyl-3-cyclohexen-1-yl)-alkanone compound according to Formula I wherein $R^1$ and $R^2$ are each independently $C_1$-$C_4$ alkyl, and $R^3$, $R^4$, $R^5$, $R^6$, $R^7$, and $R^8$ are each independently selected from the group consisting of H and $C_1$-$C_4$ alkyl; and epimerizing the first isomer of the 1-(2-alkyl-3-cyclohexen-1-yl)-alkanone with a metal alkoxide base selected from the group consisting of potassium tert-butoxide, lithium tert-butoxide, titanium tetra-n-butoxide, titanium tetra-iso-propoxide, and mixtures of any thereof to form a second isomer of the 1-(2-alkyl-3-cyclohexen-1-yl)-alkanone.

2. The process of claim 1, wherein the 1-(2-alkyl-3-cyclohexen-1-yl)-alkanone is a product of a Diels-Alder-type [4+2] cycloaddition reaction, and the first isomer of the 1-(2-alkyl-3-cyclohexen-1-yl)-alkanone is the kinetically favored isomer in the Diels-Alder-type [4+2] cycloaddition reaction and the second isomer is the thermodynamically favored isomer in the Diels-Alder-type [4+2] cycloaddition reaction.

3. The process of claim 1, wherein the first isomer is a 1,2-cis-isomer of the 1-(2-alkyl-3-cyclohexen-1-yl)-alkanone according to Formula II and the second isomer is a 1,2-trans-isomer of the 1-(2-alkyl-3-cyclohexen-1-yl)-alkanone according to Formula III $$\text{III}$$

(structure: cyclohexene with R⁶, R⁷, R⁸ at top, R⁵, R⁴, R³ at bottom/left, H and C(=O)R¹ with ....R² substituents)

4. The process of claim 3, wherein the metal alkoxide base is potassium tert-butoxide.

5. The process of claim 4, wherein epimerizing the first isomer to the second isomer comprises reacting the first isomer with potassium tert-butoxide in an organic solvent at a temperature ranging from about 25° C. to about 66° C.

6. The process of claim 1, further comprising:
condensing the second isomer of the 1-(2-alkyl-3-cyclohexen-1-yl)-alkanone with an aldehyde followed by elimination of water to form a first aldol condensation product.

7. The process of claim 6, wherein the elimination of water produces a mixture of the first aldol condensation product and a second aldol condensation product, wherein the first aldol condensation product is a α,β-unsaturated ketone and the second aldol condensation product is a constitutional isomer of the first aldol condensation product,
the process further comprising isomerizing the second aldol condensation product to the first aldol condensation product.

8. The process of claim 6, wherein the epimerizing step and the condensing step are performed in a single reactor.

9. The process of claim 1, wherein the first isomer of 1-(2-alkyl-3-cyclohexen-1-yl)-alkanone is cis-1-(2,6,6-trimethylcyclohex-3-en-1-yl)-ethanone and the second isomer is trans-1-(2,6,6-trimethylcyclohex-3-en-1-yl)-ethanone.

10. The process of claim 9, further comprising:
condensing the trans-1-(2,6,6-trimethylcyclohex-3-en-1-yl)ethanone with an aldehyde followed by elimination of water to form an aldol condensation product.

11. The process of claim 10, wherein the aldehyde is acetaldehyde and the aldol condensation product is (±)-δ-damascone.

12. A process for producing an aldol condensation product comprising:
epimerizing a first cis/trans isomer of a 1-(2-alkyl-3-cyclohexen-1-yl)-alkanone according to Formula I:

$$\text{I}$$

(structure: cyclohexene with R⁶, R⁷, R⁸, R⁵, R⁴, R³ substituents, H, C(=O)R¹ and R²)

with potassium tert-butoxide to form a second cis/trans isomer of the 1-(2-alkyl-3-cyclohexen-1-yl)-alkanone, where R¹ and R² are each independently $C_1$-$C_4$ alkyl, and R³, R⁴, R⁵, R⁶, R⁷, and R⁸ are each independently selected from the group consisting of H and $C_1$-$C_4$ alkyl; and
condensing the second isomer of the 1-(2-alkyl-3-cyclohexen-1-yl)-alkanone with an aldehyde followed by elimination of water to form a first aldol condensation product.

13. The process of claim 12, wherein the first cis/trans isomer is a 1,2-cis-isomer of the 1-(2-alkyl-3-cyclohexen-1-yl)-alkanone and the second cis/trans isomer is a 1,2-trans-isomer of the 1-alkyl ketone-2-alkyl substituted-3-cyclohexene.

14. The process of claim 12, wherein the first cis/trans isomer of 1-(2-alkyl-3-cyclohexen-1-yl)-alkanone is cis-1-(2,6,6-trimethylcyclohex-3-en-1-yl)ethanone and the second cis/trans isomer is trans-1-(2,6,6-trimethylcyclohex-3-en-1-yl)ethanone.

15. The process of claim 14, wherein the aldehyde is acetaldehyde and the first aldol condensation product (±)-δ-damascone.

16. The process of claim 12, wherein the epimerizing step and the condensing step are performed in a single reactor.

17. A single reactor process for the production of a cyclohexene product comprising:
epimerizing a 1,2-cis-isomer of a 1-(2-alkyl-3-cyclohexen-1-yl)-alkanone with potassium tert-butoxide to form a 1,2-trans-isomer of the 1-(2-alkyl-3-cyclohexen-1-yl)-alkanone; and
condensing the 1,2-trans-isomer of the 1-(2-alkyl-3-cyclohexen-1-yl)-alkanone with an aldehyde followed by elimination of water to form a first aldol condensation product,
wherein the epimerizing step and the condensing step are performed in a single reactor.

18. The single reactor process of claim 17, wherein the 1,2-cis-isomer of the 1-(2-alkyl-3-cyclohexen-1-yl)-alkanone is cis-1-(2,6,6-trimethylcyclohex-3-en-1-yl)-ethanone and the 1,2-trans-isomer of the 1-(2-alkyl-3-cyclohexen-1-yl)-alkanone is trans-1-(2,6,6-trimethylcyclohex-3-en-1-yl)-ethanone.

19. The single reactor process of claim 18, wherein the aldehyde is acetaldehyde and the first aldol condensation product is (±)-δ-damascone.

20. The single reactor process of claim 17, further comprising:
purifying the first aldol condensation product by distillation.

21. The single reactor process of claim 17, wherein the 1,2-cis-isomer of the 1-(2-alkyl-3-cyclohexen-1-yl)-alkanone is a product of a Lewis acid catalyzed Diels-Alder-type [4+2] cycloaddition reaction in an ionic liquid.

* * * * *